United States Patent [19]

Radebaugh

[11] Patent Number: Plant 6,484

[45] Date of Patent: Dec. 20, 1988

[54] POINSETTIA PLANT NAMED CHRISTMAS BLUSH

[76] Inventor: James D. Radebaugh, 1108 Bentley Rd., Freeland, Md. 21053

[21] Appl. No.: 25,205

[22] Filed: Mar. 12, 1987

[51] Int. Cl.[4] ..... A01H 5/00

[52] U.S. Cl. ..... Plt./86

[58] Field of Search ..... Plt./86

*Primary Examiner*—James R. Feyrer

*Attorney, Agent, or Firm*—Schwartz, Jeffery, Schwaab, Mack, Blumenthal & Evans

[57] ABSTRACT

A Poinsettia named Christmas Blush characterized by its salmon bract color, which fades on maturity to a salmon-orange color, with the bracts being bicolored during the maturing process.

1 Drawing Sheet

1

The present invention relates to a new and distinct cultivar of poinsettia plant known by the cultivar name Christmas Blush, and botanically known as *Euphorbia pulcherrima.*

Christmas Blush was discovered as a mutation by applicant on Dec. 15, 1985 in a commercial greenhouse in Freeland, Md., growing in a bed of the parent cultivar V-14 Pink, disclosed in U.S. Plant Pat. No. 4,808. The new cultivar was immediately recognizable by its lighter salmon pink bract color, as opposed to the deeper pink bract color of the parent.

The first act of asexual reproduction of Christmas Blush was accomplished when vegetative cuttings were taken from the initial selection on July 8, 1986 in a controlled environment in Radebaugh's North greenhouses in Freeland, Md. by applicant. Horticultural examination of selected units initiated after propagation has demonstrated that the combination of characteristics as herein disclosed for Christmas Blush are firmly fixed and are retained through successive generations of asexual reproduction.

Christmas Blush has not been observed under all possible environmental conditions. The phenotype may vary significantly with variations in environment such as temperature, light intensity, and day length. The following observations, measurements and comparisons describe plants grown in Radebaugh's North under greenhouse conditions which approximate those generally used in commercial practice.

The traits of Christmas Blush described below have been repeatedly observed and are determined to be basic characteristics of Christmas Blush, which in combination distinguish this poinsettia as a new and distinct cultivar. The new cultivar is very similar in growth and plant characteristics to its parent, to the extent determinable at this time. The distinguishing feature of Christmas Blush is its bract color, which is a unique soft shell pink color with some deeper tones in the center of the bracts. The older exterior bracts seem to lighten with maturity to a creamy salmon shade of pink.

The accompanying photographic drawings show typical inflorescence and foliage characteristics of Christmas Blush, with colors being as nearly true as possible with illustrations of this type. The photograph at the top of the drawing sheet is a perspective view of the new cultivar, and the photograph at the bottom of the sheet is an enlarged showing of the bracts and cyathias. The photographs were taken in early January in late afternoon in Freeland, Md.

2

In the following description color references are made to The Royal Horticultural Society Colour Chart. The color values were determined at approximately 11:00 a.m. on Jan. 29, 1987 under natural light conditions at Alexandria, Va.

Classification:

*Botanical.*—*Euphorbia pulcherrima.*

*Commercial.*—Poinsettia.

Parentage: Mutation of V-14 Pink.

Plant description:

(A) *Form.*—Typical poinsettia, with upright, strong stems.

(B) *Growth habit.*—Vigorous, average branching and breaking; strong plant.

(C) *Rooting.*—Excellent, in 18–21 days with medium temperatures of about 22° C.; sanitary conditions must be provided.

(D) *Blooming season.*—Natural season at 15° C.–20° C. approximately November 20–December 1.

(E) *Blooming habit.*—Floriferous; keeping quality is excellent, with bracts keeping until mid or late February under average (15°–20° C.) temperature and proper care.

Foliage:

(A) *Size.*—Short petiole, leaf blade 6–8 cm wide and 10–14 cm long.

(B) *Quantity.*—Average.

(C) *Color.*—New foliage: Upper side, 144B; under side, 144C-D. Mature foliage: Upper side, 137A; under side 137C. Leaf petiole: Approximately 151A.

(D) *Shape.*—Generally oval, tip acute to acuminate.

(E) *Texture.*—Typical.

(F) *Edge of margin.*—Slightly crenated but generally smooth.

(G) *Disease resistance.*—No disease noted to date.

Flowers (Cyathia):

(A) *Borne.*—Very dense inflorescence — clustered. Color approximately 13A.

(B) *Quantity.*—As many as 10–16 in tight form.

(C) *Continuity.*—Average to good holding quality under home conditions. Mature cyathias 4 mm in diameter, 12 mm long.

Bracts:

(A) *Size.*—Older initial bracts mature to 16–18 cm long and 10–12 cm wide. Young bracts are approximately 4–6 cm wide and 10–12 cm long.

(B) *Quantity.*—Several layers of bracts provide large overall blooms and excellent keeping quality.

(C) *Color.*—Immature new bracts 38A, maturing to 38B; this bract color is maintained 2–3 weeks at which time mature bracts will gradually and randomly fade to approximately 29D, a salmon-orange color. During this maturing process, bracts are bicolored, showing both 38B and 29D, until becoming almost entirely 29D. In conditions of continuous or above normal sun, and upon further maturity, bracts will fade even further to approximately 20D.

Reproductive organs: Typical for Poinsettias.

I claim:

1. A new and distinct cultivar of Poinsettia named Christmas Blush, as illustrated and described, and particularly characterized by its salmon bract color, which fades on maturity to a salmon-orange color, with the bracts being bicolored during the maturing process.

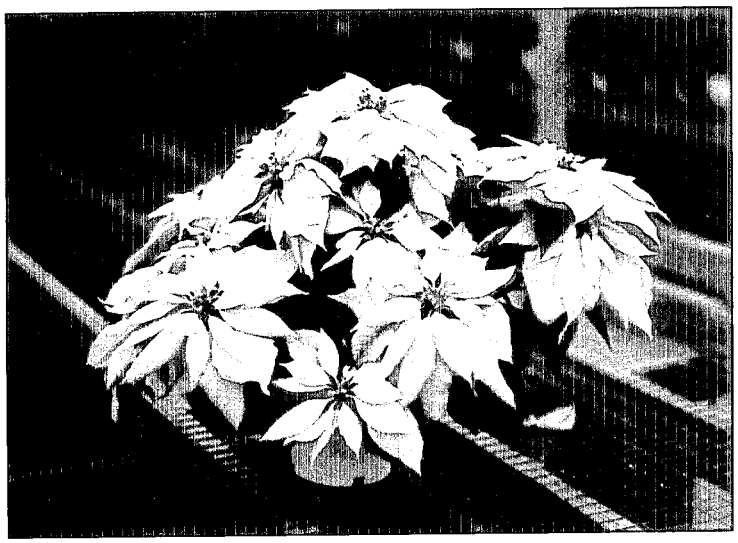
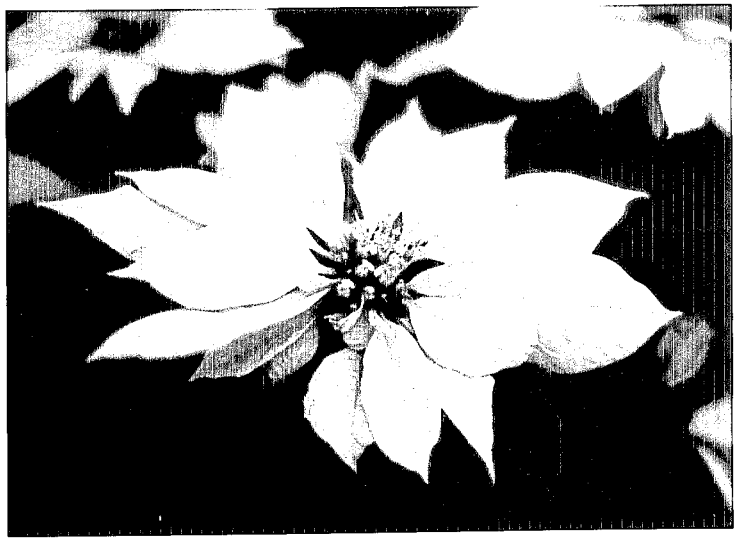

* * * * *